United States Patent [19]

Miller et al.

[11] Patent Number: 5,140,054

[45] Date of Patent: Aug. 18, 1992

[54] RADIATION CURABLE POLYPROPENYL ETHER RESINS

[75] Inventors: Mark M. Miller, Ridgewood; Jeffrey S. Plotkin, Monsey, N.Y.

[73] Assignee: ISP Investments Inc., Wilmington, Del.

[21] Appl. No.: 756,715

[22] Filed: Sep. 9, 1991

[51] Int. Cl.$^5$ .................. C08F 2/50; C08F 26/02; C08F 126/02; C08C 261/00

[52] U.S. Cl. ..................... 522/31; 522/170; 522/174; 522/97; 526/301; 560/26; 560/158

[58] Field of Search .................. 560/26, 158; 522/170, 522/174, 97, 31; 526/301

[56] References Cited

U.S. PATENT DOCUMENTS

| | | | |
|---|---|---|---|
| 2,464,519 | 10/1945 | Lichty et al. | 560/158 |
| 3,887,607 | 6/1975 | Kehr et al. | 560/26 |
| 3,950,285 | 4/1976 | Wolgemuth | 560/26 |
| 4,751,273 | 6/1988 | Lapin et al. | 560/158 |
| 5,045,572 | 9/1991 | Plotkin et al. | 522/170 |
| 5,055,357 | 10/1991 | Plotkin et al. | 522/170 |

*Primary Examiner*—Marion E. McCamish
*Assistant Examiner*—Susan Berman
*Attorney, Agent, or Firm*—Marilyn J. Maue; Joshua J. Ward

[57] ABSTRACT

This invention relates to a polypropenyl ether having the formula

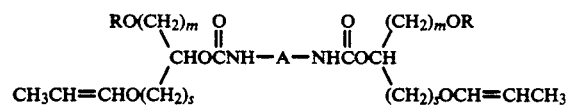

wherein m and s each independently have a value of from 1 to 6; R is alkyl or phenyl optionally substituted with lower alkyl or halogen; A is $C_2$ to $C_{12}$ alkylene or $C_6$ to $C_{22}$ aryl, both optionally substituted with lower alkyl, haloalkyl, halogen or phenyl.

15 Claims, No Drawings

RADIATION CURABLE POLYPROPENYL ETHER RESINS

BACKGROUND OF THE INVENTION

It is known that certain acrylate and urethane coating materials can be cured thermally or by radiation in the presence of a free-radical photoinitiator but that they do not lend themselves to cationically induced polymerization. It is well recognized that thermal curing is not cost efficient and that radiation curing in free-radical systems is oxygen inhibited, thus requiring an inert atmosphere or the minimizing affect of a hydrogen donating component. However, the presence of a hydrogen donating component is not completely satisfactory since such components significantly reduce the rate of reaction. Also, it has been found that polymerization or curing in free radical systems ceases almost immediately upon removal from the source of radiation; thus, the cured product often contains significant amounts of unpolymerized components. Accordingly, it is an aim of research to develop monomers or oligomers which provide stable formulations with the above polymerizable materials while incorporating their beneficial properties in the finished product. Additionally, it is desirable that such monomers or their oligomers be amenable to radiation curing at a rapid rate under mild temperature conditions by cationically induced polymerization which is not oxygen inhibited and which permits continued polymerization after removal from the source of radiation exposure. Further, it would be beneficial if the monomer or oligomer, when used as a diluent for such polymerizable materials, would be capable of minimizing undesirable properties of certain coating materials, such as the acrylate monomers which are known skin irritants.

Accordingly, it is an object of the present invention to overcome the above deficiencies and to provide polypropenyl ethers which are readily polymerizable to thermally stable compounds having superior coating properties and which provide films having good adhesion and high resistance to chemical attack.

Another object of this invention is to provide an economical and commercially feasible process for preparing the polypropenyl ethers of this invention.

Still another object is to provide coatings and finishes for adhesion resistant surfaces such as metal and glass, which coatings are not subject to coloration or extended periods of use.

These and many other objects of the invention will become apparent from the following description and disclosure.

THE INVENTION

In accordance with this invention there is provided a radiation curable, polypropenyl ether having the formula

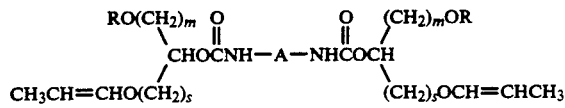

wherein m and s each independently have a value of from 1 to 6; R is alkyl or phenyl optionally substituted with lower alkyl or halogen and A is $C_2$ to $C_{12}$ alkylene or $C_6$ to $C_{22}$ aryl, both groups optionally substituted with lower alkyl, haloalkyl, halogen or phenyl.

The divalent A radical includes for example, linear, branched and cyclic $C_2$ to $C_{12}$ alkylene radicals and mono-, di- and tri- cyclic aryl radicals, specific examples of which include butylene; hexylene; cyclohexylene; dicyclohexylene; cyclobutylene; 2,4-dimethyl hexylene; 2,2,4-trimethyl hexylene; decylene; dodecylene; 2,4,6-trimethyl octylene; phenylene; naphthylene; tolylene; xylylene; bisphenylene;

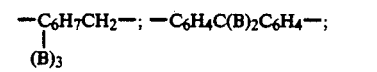

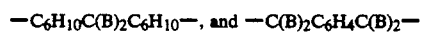

where B is hydrogen or methyl; which radicals may be additionally substituted with a halogen, haloalkyl, lower alkyl or phenyl radical.

The above polypropenyl ethers can be prepared according to the following equation:

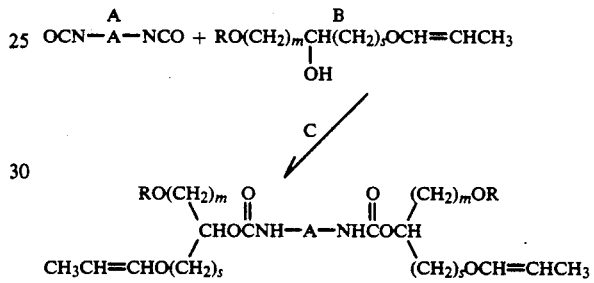

wherein m, s, A and R are as defined.

Reactant B is prepared by any convenient method and is preferably obtained as the product of the reaction between an alk-1-enyl glycidyl ether and an excess of an aliphatic alcohol or phenol corresponding to the formula ROH where R is as defined above. This reaction is carried out in the presence of between about 1 and about 2 wt. % of a base catalyst, e.g. a sodium or potassium methoxide, butoxide or hydroxide.

The reaction of the present invention according to the above equation is carried out by forming a liquid mixture of compounds A and B in a mole ratio of between about 1:2 and about 1:4, preferably 1:2. Suitable examples of reactant A include chlorobenzene diisocyanate; dichloro benzenediisocyanate; diisocyanto benzene; diisocyanto toluene; diisocyanto xylene; bromobenzene diisocyanate; fluorobenzene diisocyanate; bis(phenylisocyanate); bis(2-methyl-phenylisocyanate); bis(2-chloromethyl-phenylisocyanate); bis-(isocyanatomethyl ethyl benzene) TMXDI; 1,1-methylene bis(isocyanatocyclohexane); toluene diisocyanate, TDI; 4,4'-methylenediphenyl diisocyanate, MDI; 4,4'-methylene dicyclohexyldiisocyanate; naphthylene diisocyanate; 1,6-hexamethylene diisocyanate; isopropane diisocyanate; cyclohexane diisocyanate; 5-iso-cyanato-1-(isocyanatomethyl)-1,3,3-trimethyl cyclohexane; bis(isocyanatophenyl) isopropane; trimethyl hexamethylene diisocyanate; 1,4-diisocyanato diphenyl; 2,2-bis(4-isocyanato phenyl) propane, bis(4-isocyanato phenyl) methane, etc.

Examples of coreactant B include the propenyl ethers of 2-hydroxy butyl methyl ether, 6-hydroxydecyl methyl ether, 4-hydroxyoctyl methyl ether, 2-hydroxypropyl methyl ether, 3-hydroxybutyl methyl ether and the like.

The reaction is carried out in the absence or in the presence of a base catalyst such as, e.g. dibutyl tin dilaurate, diazabicyclo octane, triethylamine, 1,8-diazabicyclo [5.3.0]undec-7-ene, metal acetyl acetonates of manganese, vanadium, iron, cobalt, copper and chromium and the like, which catalyst, when employed, is used in a concentration of between about 0.01 and 0.5 weight %, preferably between about 0.02 and about 0.3 weight %, based on total reactants.

In cases where the mixture of reactants results in a liquid having a viscosity such that good agitation becomes difficult, up to about 50 weight % of an inert solvent can be added to the mixture. Suitable solvents include toluene, xylene, benzene, methylene chloride, tetrahydrofuran; ketones such as methyl ethyl ketone, acetone, methyl isobutyl ketone, amides such as N-methylpyrrolidone, dimethylforamide and N-ethylpyrrolidone; esters such as butyrolactone and ethyl acetate or mixtures of these and the like. Where the isocyanate reactant is a solid, it is melted or dissolved in one of the above solvents or solvent mixtures before reacting.

The present reaction is effected in the liquid phase by agitating the reactants under a blanket of inert gas such as nitrogen, argon, etc. at a temperature within the range of about between about 30° and about 100° C. under atmospheric pressure. The reaction takes place over a period of from about 1 to about 20 hours. The preferred reaction conditions include a temperature of between about 50° and about 70° C. under atmospheric pressure for a period of from about 2 to 8 hours. Upon completion of the reaction in a solvent, the solvent can be recovered by evaporation under a reduced pressure and the product purified by fractional distillation.

The products of this process are useful as molding resins and highly solvent resistant adhesive coatings. The product can be applied to a glass, metal, wood, paper or other surface in a thickness of between about 0.1 to about 5 mils and cured by exposure to a source of radiation such as UV light, electon beam or laser emission or exposure to radiation rays such as X-rays, gamma-rays, etc. in the presence of an onium photoinitiator such as, for example a diaryl iodonium salt, a phenyl sulphonium salt, and the like. Curing by UV light exposure is generally effected at between about 30 and about 1,000 milli joules/cm². Radiation curing is completed in less than 1 minute, usually less than 5 seconds, most preferably less than 1 second exposure; whereas curing by heat requires a longer treatment up to about 2 hours. The present compounds provide clear, colorless, flexible films which find many applications. Additionally, the present products can be combined with up to about 50% of another monomer, such as the divinyl ether of triethylene glycol (DVE 3), the divinyl ether of cyclohexane dimethanol (CHVE), dodecyl vinyl ether or an epoxide, e.g. 3,4-epoxycyclohexyl methyl-3,4-epoxycyclo hexane carboxylate; 1,4-butanediol diglycidyl ether, etc. and, in the presence of a cationic initiator, cured by exposure to radiation so as to provide a protective coating or film.

Having thus generally described the invention, reference is now had to the accompanying examples which illustrate preferred embodiments but which are not construed as limiting to the scope of the invention as more broadly set forth above and in the appended claims.

EXAMPLE I

A. Into a 1500 cc round bottom flask equipped with a mechanical stirrer, reflux condenser and addition buret was added 800 g of methanol and 2 g of sodium methoxide. The mixture was heated to 64° C. and refluxed. To this mixture, 286 grams of propenyl glycidyl ether (PGE) was added continuously over a 2 hour period, being sure to maintain a stable reflux condition. At this point gas chromatographic analysis showed 88% conversion of PGE, however; after 2 additional hours of reflux conversion was complete. The flask was then fitted with a distillation head, and excess methanol was stripped off. The reaction product 1-propenyloxy-3-methoxy-2-propanol was then purified by fractional distillation and 310 g of 98.6% pure product was recovered. Structure was confirmed by infra red and H¹NMR spectroscopy.

B. Into a liter sealed reactor was introduced 53.37 g (0.33 mole) of benzene 2,4-diisocyanate (BDI) dissolved in 100 cc of dry tetrahydrofuran under a nitrogen atmosphere, after which 97.24 g (0.66 moles) of 1-propenyloxy-3-methoxy-2-propanol was added along with 0.1 g of dibutyltin dilaurate (DBTD) at a controlled rate such that the reaction exotherm did not exceed 60° C. In this case the addition was effected over a period of 15 minutes. The reaction was monitored by volumetric isocyanate analysis, and proceeded to completion in 3 hours at 50° C. The solvent was then removed under vacuum and the resulting viscous clear liquid (150.2 g) of

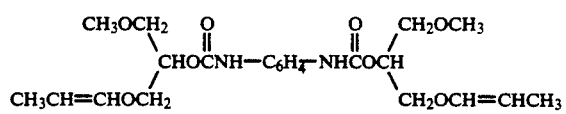

was recovered and the product confirmed by H¹NMR and Fourier Transform Infra red spectrometry.

EXAMPLE II

The product of Examples I was used to make a radiation curable formulation by containing 49% of said product 49% divinyl ether of triethylene glycol and 2% of triphenyl sulfonium salt initiator. The formulation was coated on an aluminum panel and cured using a 400 mJ/cm² PPG model QC-1202A/N U.V. processor. The coating performance of said cured polymer was compared to those of a commercial urethane vinyl ether oligomer CB#2 and Epon-828 (epoxide). Results are summarized in the following table.

TABLE

| OLIGOMER | COATING THICKNESS | MAX. CURE SPEED (fpm) | PENCIL HARDNESS | | ADHESION % | | MANDRELL BEND | MEK RUBS | |
|---|---|---|---|---|---|---|---|---|---|
| Product of Example I | 0.31 | 700 | 2H | 2H | 0 | 100 | ↓ ↓ | 2 | 2 |
| CB #2 89* | 0.30 | 700 | 2B | 2H | 0 | 100 | 3/16 ↓ | 6 | 82 |
| Epon-828** | 0.33 | 500 | 2H | 2H | 100 | 100 | ↓ ↓ | 1 | 28 |
| Product of Example I | 1.50 | 700 | <4B | H | 0 | 0 | ↓ ↓ | 95 | 75 |

TABLE-continued

| OLIGOMER | COATING THICKNESS | MAX. CURE SPEED (fpm) | PENCIL HARDNESS | | ADHESION % | | MANDRELL BEND | | MEK RUBS | |
|---|---|---|---|---|---|---|---|---|---|---|
| CB #2 89 | 1.41 | 500 | <4B | 2B | 0 | 0 | 3/16 | 3/16 | 69 | >100 |
| Epon-828 | 1.61 | 300 | <4B | 2H | 0 | 100 | 3/16 | 1 | 23 | >100 |

*vinyl ether terminated urethane isocyanate oligomer
**the diglycidyl ether of bisphenol A

EXAMPLE III

Into a 1-liter sealed reactor was introduced 58.00 g (0.33 mole) of toluene 2,4-diisocyanate (TDI) dissolved in 100 cc of dry tetrahydrofuran under a nitrogen atmosphere, after which 97.24 g (0.66 moles) of 1-propenyloxy-3-methoxy-2-propanol was added along with 0.1 g of dibutyltin dilaurate (DBTD) at a controlled rate such that the reaction exotherm did not exceed 60° C. In this case the addition was effected over a period of 15 minutes. The reaction was monitored by volumetric isocyanate analysis, and proceeded to completion in 3 hours at 50° C. The solvent was then removed under vacuum and the resulting viscous clear liquid (155.3 g) of $$CH_3OCH_2\diagdown CHOCNH-\underset{CH_3}{\underset{|}{\bigcirc}}-NHCOCH\diagdown CH_2OCH_3$$
$$CH_3CH=CHOCH_2 \diagup \qquad \qquad \diagup CH_2OCH=CHCH_3$$

was recovered and the product confirmed by H¹NMR and Fourier Transform Infra red spectrometry.

EXAMPLE IV

Into a 1-liter sealed reactor was introduced 83.34 g (0.33 mole) of methylene di-p-phenyl diisocyanate dissolved in 100 cc of dry tetrahydrofuran under a nitrogen atmosphere, after which 97.24 g (0.66 moles) of 1-propenyloxy-3-methoxy-2-propanol was added along with 0.1 g of dibutyltin dilaurate (DBTD) at a controlled rate such that the reaction exotherm did not exceed 60° C. In this case the addition was effected over a period of 15 minutes. The reaction was monitored by volumetric isocyanate analysis, and proceeded to completion in 3 hours at 50° C. The solvent was then removed under vacuum and the resulting viscous clear liquid (180.7 g) of $$CH_3OCH_2\diagdown CHOCNH-\bigcirc-CH_2-\bigcirc-NHCOCH\diagdown CH_2OCH_3$$
$$CH_3CH=CHOCH_2\diagup \qquad \qquad \diagup CH_2OCH=CHCH_3$$

was recovered and the product confirmed by H¹NMR and Fourier Transform Infra red spectrometry.

EXAMPLE V

Into a 1 liter sealed reactor was introduced 92.67 g (0.33 mole) of 2,2-bis(4-isocyanato phenyl) propane dissolved in 100 cc of dry tetrahydrofuran under a nitrogen atmosphere, after which 97.24 g (0.66 moles) of 1-propenyloxy-3-methoxy-2-propanol was added along with 0.1 g of dibutyltin dilaurate (DBTD) at a controlled rate such that the reaction exotherm did not exceed 60° C. In this case the addition was effected over a period of 15 minutes. The reaction was monitored by volumetric isocyanate analysis, and proceeded to completion in 3 hours at 50° C. The solvent was then removed under vacuum and the resulting viscous clear liquid (190.0 g) of $$CH_3OCH_2\diagdown \qquad CH_3 \qquad CH_2OCH_3$$
$$\phantom{CH_3OCH_2}CHOCNH-\bigcirc-\underset{CH_3}{\overset{|}{C}}-\bigcirc-NHCOCH$$
$$CH_3CH=CHOCH_2\diagup \qquad \qquad \diagup CH_2OCH=CHCH_3$$

was recovered and the product confirmed oy H¹NMR and Fourier Transform Infra red spectrometry.

EXAMPLE VI

Into a 1-liter sealed reactor was introduced 70.63 g (0.33 mole) of diisocyanato dibutyl ether dissolved in 100 cc of dry tetrahydrofuran under a nitrogen atmosphere, after which 97.24 g (0.66 moles) of 1-propenyloxy-3-methoxy-2-propanol was added along with 0.1 g of dibutyltin dilaurate (DBTD) at a controlled rate such that the reaction exotherm did not exceed 60° C. In this case the addition was effected over a period of 15 minutes. The reaction was monitored by volumetric isocyanate analysis, and proceeded to completion in 3 hours at 50° C. The solvent was then removed under vacuum and the resulting viscous clear liquid (168.0 g) of $$CH_3OCH_2\diagdown \qquad O \qquad O \qquad CH_2OCH_3$$
$$\phantom{CH_3OCH_2}CHOCNH-C_4H_8OC_4H_8-NHCOCH$$
$$CH_3CH=CHOCH_2\diagup \qquad \qquad \diagup CH_2OCH=CHCH_3$$

was recovered and the product confirmed by H¹NMR and Fourier Transform Infra red spectrometry.

What is claimed is:
1. The polypropenyl ether having the formula

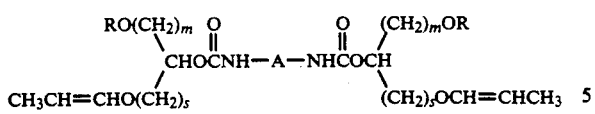

wherein m and s each independently have a value of from 1 to 6; R is alkyl or phenyl optionally substituted with lower alkyl or halogen; A is $C_2$ to $C_{12}$ alkylene or $C_6$ to $C_{22}$ aryl, which alkylene or aryl is optionally substituted with lower alkyl, haloalkyl, halogen or phenyl.

2. The polypropenyl ether of claim 1 wherein R is methyl and m and s have a value of from 1 to 2.

3. The polypropenyl ether of claim 1 which is

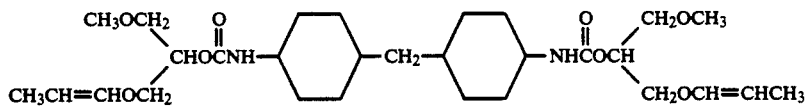

4. The polypropenyl ether of claim 1 which is

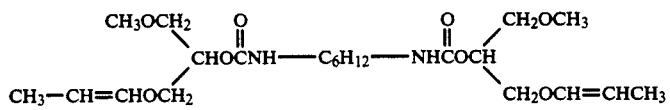

5. The polypropenyl ether of claim 1 which is

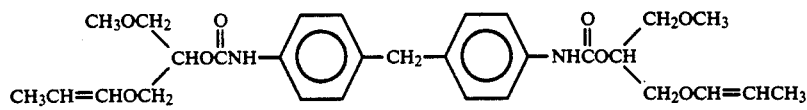

6. The polypropenyl ether of claim 1 which is

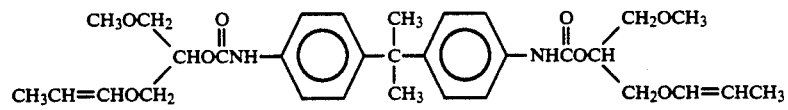

7. The polypropenyl ether of claim 1 which is

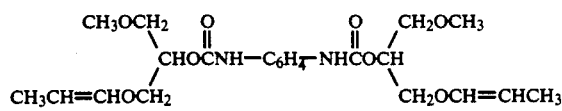

8. The polypropenyl ether of claim 1 which is

9. The cationically curable composition comprising the polypropenyl ether of claim 1 and between about 0.1 and about 4 wt. % of an onium salt initiator.

10. The composition of claim 9 wherein the onium salt is a triphenyl sulfonium salt.

11. The composition of claim 9 wherein the onium salt is a diphenyl iodonium salt.

12. The composition of claim 9 which additionally contains up to 50% of an ethylenically unsaturated comonomer.

13. The composition of claim 12 wherein the ethylenically unsaturated comonomer is the divinyl ether of triethylene glycol.

14. The composition of claim 9 which additionally contains up to 50% of an epoxy ether.

15. The composition of claim 14 wherein the epoxy ether is 1,4-butanediol diglycidyl ether.

* * * * *